(12) United States Patent
Grove

(10) Patent No.: US 7,289,634 B2
(45) Date of Patent: Oct. 30, 2007

(54) ELECTRONIC STETHOSCOPE MEASUREMENT SYSTEM AND METHOD

(75) Inventor: Deborah M Grove, North Brunswick, NJ (US)

(73) Assignee: Zargis Medical Corporation, Princeton, NJ (US)

(*) Notice: Subject to any disclaimer, the term of this patent is extended or adjusted under 35 U.S.C. 154(b) by 889 days.

(21) Appl. No.: 10/715,996

(22) Filed: Nov. 18, 2003

(65) Prior Publication Data

US 2004/0105556 A1  Jun. 3, 2004

Related U.S. Application Data

(60) Provisional application No. 60/427,160, filed on Nov. 18, 2002.

(51) Int. Cl.
*A61B 7/04* (2006.01)
(52) U.S. Cl. .......................... 381/67; 434/266
(58) Field of Classification Search ............... 381/67; 181/131; 600/528, 586; 434/266
See application file for complete search history.

(56) References Cited

U.S. PATENT DOCUMENTS

| | | | | |
|---|---|---|---|---|
| 3,055,356 A | * | 9/1962 | Chouinard | 310/23 |
| 3,662,076 A | * | 5/1972 | Gordon et al. | 434/266 |
| 3,665,087 A | * | 5/1972 | Poylo | 434/266 |
| 3,888,020 A | * | 6/1975 | Krause | 434/266 |
| 3,947,974 A | * | 4/1976 | Gordon et al. | 434/266 |
| 6,220,866 B1 | * | 4/2001 | Amend et al. | 434/266 |

OTHER PUBLICATIONS

Dale Groom M.D. et al., The Effect of Background Noise on Cardiac Auscultation, The American Heart Journal, Nov. 1956, pp. 781-790, vol. 53, No. 5.
John R. Kindig, M.D. et al., Acoustical performance of the stethoscope: A comparative analysis, The American Heart Journal, Aug. 1982, pp. 269-275, vol. 104, No. 2, Part 1, The C.V. Mosby Co.
K. E. Latimer, The Calibration of Stethoscopes and Phonocardiographic Microphones, Proc. 3rd World and 9th Europ. Congr. Ballistocard. and Cardiovasc. Dynamics, Sofia 1973. Bibl. cardiol. 33: 87-90.
Paul Y. Ertel et al., Stethoscope Acoustics and the Engineer: Concepts and Problems, Journal of the Audio Engineering Society, Mar. 1971, pp. 182-186, vol. 19, No. 3.

(Continued)

*Primary Examiner*—Vivian Chin
*Assistant Examiner*—Jason Kurr
(74) *Attorney, Agent, or Firm*—RatnerPrestia

(57) ABSTRACT

A method and apparatus for characterizing the response of an electronic stethoscope. The sensor of the electronic stethoscope is held in contact with a test surface of a phantom. A shaker, which is coupled to a stinger rod that extends inside the phantom, is driven to produce internal vibrations in the phantom. Surface motion of the test surface of the phantom is measured using a surface accelerometer coupled to the test surface. Vibrations from the phantom are detected and an electric signal based on the detected vibrations is generated with the electronic stethoscope. A surface transfer function is calculated based on the measured surface motion and the electric signal to characterize the response of the electronic stethoscope.

28 Claims, 3 Drawing Sheets

OTHER PUBLICATIONS

Maurice B. Rappaport et al., The Effects of Tubing Bore on Stethoscope Efficiency, The American Heart Journal, Jun. 11, 1951, pp. 605-609.

Maurice B. Rappaport et al., Physiologic and Physical Laws that Govern Auscultation, and Their Clinical Application, The American Heart Journal, Mar. 1941, pp. 257-318, vol. 21, No. 3.

T. J. Royston et al., Excitation and propagation of surface waves on viscoelastic half-space with application to medical diagnosis, Journal of Acoustical Society of America, Dec. 1999, pp. 3678-3686, 106(6).

T. J. Royston et al., Modeling sound transmission through the pulmonary system and chest with application to diagnosis of a collapsed lung, Journal of Acoustical Society of America, Apr. 2002, pp. 1931-1946, 111(4).

Vasant Padmanabhan et al., Accelerometer Type Cardiac Transducer for Detection of Low-Level Heart Sounds, IEEE Transactions on Biomedical Engineering, Jan. 1993, pp. 21-28, vol. 40, No. 1.

Manuel Abella et al., Comparison of the acoustic properties of six popular stethoscopes, The Journal of Acoustical Society of America, Apr. 1992, pp. 2224-2228, 91(4) Pt. 1.

* cited by examiner

ELECTRONIC STETHOSCOPE MEASUREMENT SYSTEM AND METHOD

This application is related to and claims the benefit of U.S. Provisional Application No. 60/427,160 entitled A PROPOSAL FOR STETHOSCOPE MEASUREMENT SYSTEM FOR ZARGIS MEDICAL CORPORATION filed on Nov. 18, 2002.

FIELD OF THE INVENTION

The present invention relates to the field of systems and methods for characterizing electronic stethoscopes, specifically with respect to sounds within the thorax of a subject.

BACKGROUND OF THE INVENTION

Auscultation of the heart is a well-defined and standard component of the physical examinations of patients. It is typically performed with a commercially available stethoscope. Physicians perform auscultation by listening to heart sounds desirably, in sequence, at a set of well-defined sites on the chest surfaces. These sites are typically defined with reference to anatomical landmarks, such as the second intercostal space on the left, etc. They may also be defined based on the heart valve preferentially heard at that location (i.e., aortic, pulmonic, etc.). Additionally, auscultation can be carried out with the patient in different postures, or while executing various maneuvers that are designed to enhance or suppress certain murmurs.

Auscultation of the heart is a difficult procedure, involving significant training. Stethoscopes transfer only a small fraction of the acoustic signal at the chest surface to the listener's ears and filter the cardiac acoustic signal in the process. A significant portion of the signal energy in heart sounds is at frequencies below the frequency range of human hearing, and this situation only tends to worsen with increased age of the listener. Thus, as a physician's auscultatory skill increases, his hearing may still limit his ability.

Also, auscultation relies on determining the correct sequence of brief events that are closely spaced in time, a determination that may be difficult for human listeners. Furthermore, auscultation relies on determining the correspondence of the primary heart sounds with the length of the systolic and diastolic phase of the heart. This becomes more difficult when the systolic and diastolic intervals are more equal, which typically occurs at elevated heart rates.

The practice and teaching of the clinical skill of auscultation of the heart has declined among physicians. Learning auscultation is complicated by the reliance of diagnostic instructional manuals that rely on subjective descriptions of heart sounds, which require much practice to appreciate. Recent tests have demonstrated that many physicians can reliably identify only a small number of standard heart sounds and murmurs, as described by Burdick et al., in "Physical Diagnosis Skills of Physicians in Training: A Focused Assessment," Acad. Emerg. Med., 2(7), pp. 622-29, July 1995; Mangione et al., in "Cardiac Auscultatory Skills of Internal Medicine and Family Practice Trainees: A Comparison of Diagnostic Proficiency," Journal of the American Medical Association, 278(9), pp. 717-22, September 1997; and Gracely et al., in the Teaching and Practice of Cardiac Auscultation During Internal Medicine and Cardiology Training: A Nationwide Survey," Annals of Internal Medicine, 119(1), pp. 47-54, July 1993. Consequently, serious heart murmurs in many patients may go undetected by physicians relying on standard auscultation technique.

This decline in auscultation skills has led to an over-reliance on echocardiography, resulting in a large number of unnecessary and expensive diagnostic studies. Thus, economic factors have also lead to an interest in improving auscultatory screening procedures. One approach that has generated interest is the use of electronic stethoscopes. These electronic stethoscopes may improve auscultation procedures by amplifying and/or filtering sounds detected during auscultation, helping the physician to hear the important bodily sounds. The use of electronic stethoscopes in auscultation may also allow the recording of heart sounds for automated analysis to assist the physician in making a diagnosis.

Particularly, in the area of automated analysis of auscultatory data, it is important to known the characteristics of the electronic stethoscope, or other sound recording device, being used. The present invention involves an apparatus and test procedures to test the response characteristics of an electronic stethoscope.

SUMMARY OF THE INVENTION

An exemplary embodiment of the present invention is a method for characterizing the response of an electronic stethoscope. The sensor of the electronic stethoscope is held in contact with a test surface of a phantom body (hereinafter referred to as a phantom). A shaker, which is coupled to a stinger rod that extends inside the phantom, is driven to produce internal vibrations in the phantom. Surface motion of the test surface of the phantom is measured using a surface accelerometer coupled to the test surface. Vibrations from the phantom are detected and an electric signal based on the detected vibrations is generated with the electronic stethoscope. A surface transfer function is calculated based on the measured surface motion and the electric signal to characterize the response of the electronic stethoscope.

Another exemplary embodiment of the present invention is a computer readable medium adapted to instruct a general purpose computer to characterize the response of an electronic stethoscope. In this exemplary method, a test signal is generated to drive a shaker, which is coupled to a stinger rod that extends inside a phantom, whereby internal vibrations are produced in the phantom. A motion signal is received from a surface accelerometer coupled to a test surface of the phantom. An electronic stethoscope signal is received from the electronic stethoscope, which is in contact with the test surface of the phantom. A transfer function for the electronic stethoscope is calculated based on the motion signal and the signal provided by the electronic stethoscope.

A further exemplary embodiment of the present invention is an electronic stethoscope testing apparatus. The exemplary apparatus includes a phantom; a stinger rod which extends into the interior of the phantom; a shaker coupled to the stinger rod; a surface accelerometer coupled to a test surface of the phantom; an electronic stethoscope holder coupled to the phantom; and circuitry electrically coupled to the shaker, the surface accelerometer, and the electronic stethoscope to direct and analyze electronic stethoscope tests. The electronic stethoscope holder is arranged to hold a sensor of the electronic stethoscope in contact with the test surface of the phantom. The shaker provides vibrations to the phantom via the stinger rod. The surface accelerometer measures the movement of the test surface.

BRIEF DESCRIPTION OF THE DRAWINGS

The invention is best understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawing are the following figures.

DETAILED DESCRIPTION OF THE INVENTION

The present invention involves a system and method for testing electronic stethoscopes. The various operating characteristics of an electronic stethoscope determined in this testing may be useful to properly analyze heart, or other bodily, sounds detected by the electronic stethoscope as part of an automated auscultatory diagnostic support system. Of particular interest is the transfer function of the electronic stethoscope. The electronic stethoscope's transfer function represents the amplitude of the output electric signal of the electronic stethoscope versus the amplitude of surface oscillations of the body on which the auscultation is being performed, as a function of frequency. This transfer function may be used to more accurately relate the electric output signals to the actual sounds detected during auscultation procedure and, thus, allow a more certain analysis of these sounds.

Figure 1:
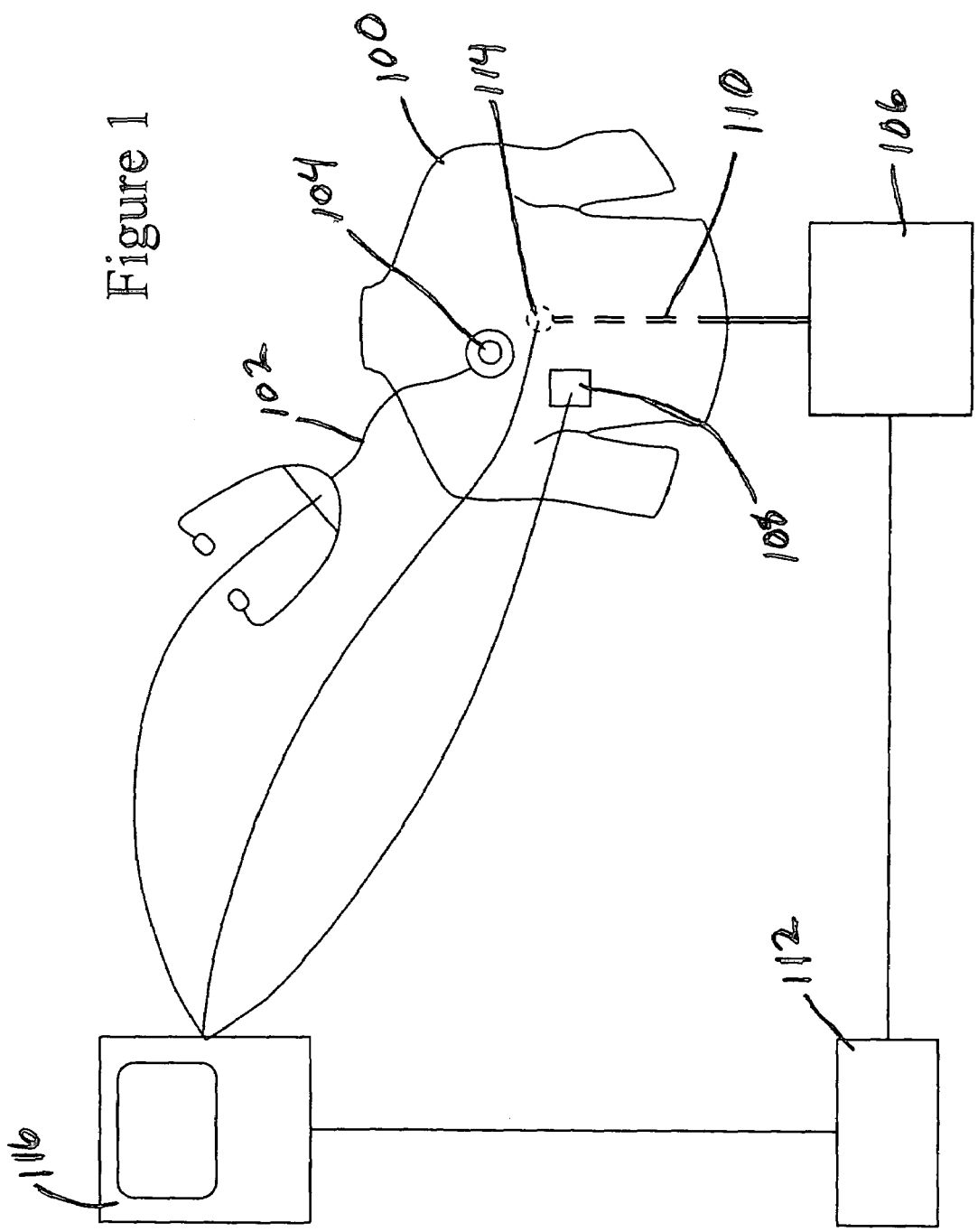
FIG. 1 is a block diagram of an exemplary electronic stethoscope testing system according to the present invention.

FIG. 1 is a block diagram that shows an exemplary embodiment of the present invention. This exemplary electronic stethoscope testing apparatus includes phantom 100, shaker 106, stinger rod 110, function generator 112, and computer 116. Surface accelerometer 108 and stinger accelerometer 114 are coupled to phantom 100 and stinger rod 110, respectively. Also coupled to phantom 100 is an electronic stethoscope holder (described below with reference to FIG. 2) to hold sensor 104 of electronic stethoscope 102 in contact with a test surface portion of phantom 100. The electronic stethoscope testing apparatus may also desirably include a substantially anechoic chamber surrounding the phantom. This anechoic chamber may reduce noise from external sound and vibrations, which may affect the test.

Signals representing heart sounds detected by electronic stethoscope 102 may be transmitted to computer 116 over a transmission line, as may signals from accelerometers 108 and 114, representing motion of the test surface of phantom 100 and stinger rod, respectively. Alternatively, any or all of these signals may be transmitted via an infrared or wireless broadcast signal.

Test control, data acquisition, and test analysis may desirably be performed by computer program instructions that control computer 116 where the computer program instructions reside on a computer-readable carrier such as a magnetic or optical disk or a radio-frequency or audio-frequency carrier wave. Although computer 116 is shown in FIG. 1 as a desktop computer, it may alternatively be a laptop computer, a personal digital assistant (PDA), or may include a local terminal with a display connected to a remote server where the analysis may occur. Computer 116 is desirably one such that the system has sound input functions with sufficient bandwidth and spectral response to enable all of the desired features of the electric signals from electronic stethoscope 102 and accelerometers 108 and 114 to be received for analysis.

Although computer 116 is mostly described herein in terms of a general-purpose computer programmed to carry out test control, data acquisition, and test analysis, it is noted that these functions, or subsets of these functions, may be carried out by other means. For example, data acquisition and analysis may be performed by a spectrum analyzer or a digital oscilloscope coupled to the accelerometers and the electronic stethoscope, and the test procedures may be controlled manually. In all cases, it is desirable that the data acquisition device, whether it is computer 116, a digital oscilloscope, or another device, have an input bandwidth that is sufficient to cover the response spectrum being tested. As this desired response spectrum typically includes infrasonic frequency, <20Hz, often as low as 5Hz, attention to the bandwidth and low frequency behavior of the data acquisition device is desirable. This is particularly true of general purpose computers, in which sound processors are not typically optimized for frequencies outside of the human hearing range.

It is also contemplated that data acquisition and test analysis could be performed by special purpose signal processing circuitry, possibly embodied in an application-specific integrated circuit (ASIC), instead of by a general purpose computer. Alternatively, preprocessing of the signals may be performed by signal processing circuitry and further analysis carried out by test analysis software instructing a general purpose computer. Preamplifiers may be desirable to amplify the electronic stethoscope and/or accelerometer signals as well. Further, an analog to digital converter coupled to accelerometers 108 and 114 and/or electronic stethoscope 102 to provide digital signal(s) to computer 116 rather than analog signals. It is noted that electronic stethoscope 102 may include also amplification and/or filtering circuitry. Desirably, this circuitry may be controlled by the tester to provide separate sets of test data, so that transfer functions for each setting may be determined.

Signals from computer 116 may be used to control function generator 112, which in turn generates a signal that drives shaker 106. Function generator 112 may be a computer controlled function generator (as shown), special purpose circuitry, or the sound processor of computer 116. An additional amplifier (not shown) may be desirable to amplify the signal. Computer control of function generator 112 may allow the phantom to be driven in a specific test sequence of oscillations, including chirps, tones, a specifically colored noise spectrum, or a substantially white noise spectrum. The desired spectrum of the frequency generator signal may be affected by the frequency spectrum of the bodily sound to be simulated. For example, a significant portion of the signal energy in heart sounds is at frequencies below 20 Hz and, thus, generation of low frequency, infrasound, in the phantom is desirable for simulating a heart sound. Also, the frequency response characteristics of shaker 106, and possibly phantom 100, may be used to help select desired spectral properties for the shaker control signal.

Alternatively, the function generator may operate independently, desirably producing a substantially white noise signal, or the tester may control the oscillation form and spectrum of the function generator signal. In this alternative embodiment, function generator 112 may not be capable of computer control.

Shaker 106 is a standard mechanical shaker designed to provide linear oscillator motion in response to an electrical signal. In this exemplary apparatus, shaker 106 shakes stinger rod 110. Phantom 100 is then caused to vibrate by stinger rod 110, which extends within the phantom so that the vibrations originate from within the phantom, rather than on the surface. The stinger rod is desirably sufficiently rigid to transmit the movements of shaker 106 into phantom 100 without flexing significantly. Alternatively, the phantom may be vibrated internally by means of a speaker, which is arranged to propagate sound waves into a cavity in the phantom, or a solenoid coupled to the interior of the phantom.

The phantom is an artificial form desirably designed to simulate a human thorax, and these internal vibrations may better simulate heart, or other internal bodily sounds. It is noted that the phantom may be designed to simulate other bodies on which auscultation may be performed, including other animal thoraxes and human or animal abdomen. Desirably, the phantom has mechanical properties, such as density and speed of sound, which are similar to those of the tissue of the body being simulated. The phantom may also be sized and shaped similarly to the desired body part, though this may be less important than the mechanical properties of density and speed of sound.

Phantom 100 may be formed by an elastic bladder of a skin-like material such as rubber, vinyl, or leather, which filled with a fluid and/or a gel. Water, various oils, methylcellulose gel, and starch solutions are a few examples of fluids or gels that may be used in the phantom. One difficulty in using a filled bladder for the phantom is placement of the stinger rod within the bladder. Therefore, a solid phantom may be desirable. A solid phantom may be formed of a single material having the desired mechanical properties, such as polyurethane, or may be a composite of several materials, simulating bone, muscle, and fat. Internal air or foam pockets simulating lungs, or other substantially hollow organs, may also be incorporated within the phantom.

Figure 2:
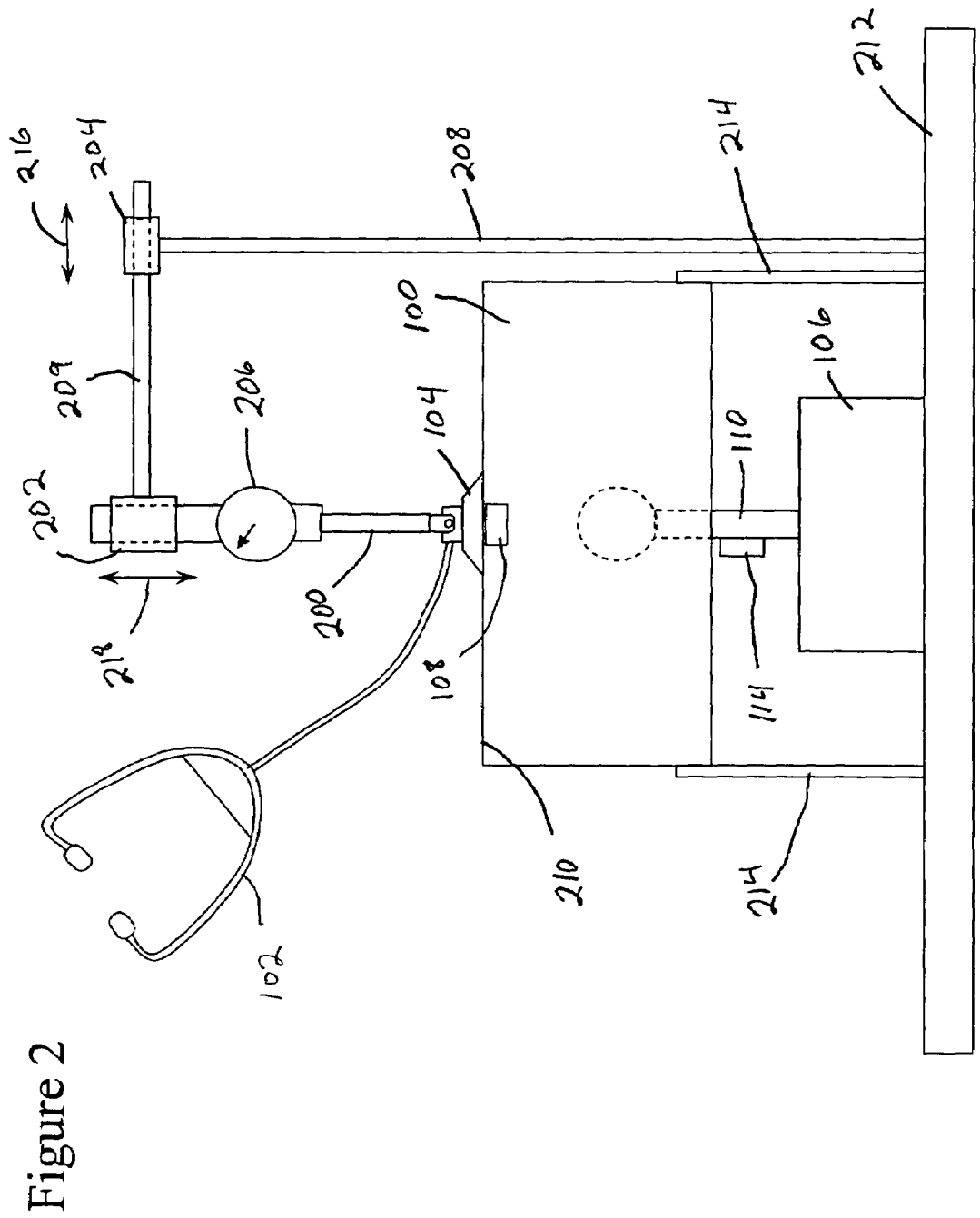
FIG. 2 is a side plan drawing illustrating an exemplary test bench structure of the present invention.

FIG. 2 illustrates a more detailed side plan view of an exemplary embodiment of the present invention including phantom 100, electronic stethoscope 102, shaker 106, stinger 110, and the associated test bench structure. To simplify examination of the exemplary mechanical structures in FIG. 2, electric connections are not included. This exemplary test bench includes shaker 106 with stinger 110 extending into phantom 100 from below, as opposed to entering on the side as in the exemplary block diagram of FIG. 1. As shown in FIG. 2, it is desirable to securely mount both phantom 100 (via braces 214) and shaker 106 to common bench 212 so that wave propagation primarily within the body of the phantom is generated, instead of the shaker primarily shaking the phantom (or shaker) as a whole. It is noted that it is desirable for common bench 212 to be sufficiently massive to significantly damp vibrations in the bench.

Electronic stethoscope holder 200 is designed to hold sensor 104 of electronic stethoscope 102 in contact with a test surface 210 of phantom 100. Electronic stethoscope holder 200 is coupled to a mounting bracket structure which is connected to common bench 212. The exemplary mounting bracket structure shown in FIG. 2 includes vertical beam 208, horizontal beam 209, vertical adjuster 202, and horizontal adjuster 204. Electronic stethoscope holder 200 and the components of the mounting bracket are desirably formed out of rigid, non-brittle materials, such as, for example, metal, plastic, or wood. Although this exemplary mounting bracket includes only one vertical beam 208, it is contemplated that the use of two vertical beams, with horizontal beam 209 extending between and coupled to both, may be desirable to increase the rigidity of the mounting bracket.

Horizontal adjuster 204 allows horizontal beam 209 to be moved as shown by arrows 216. Thus, sensor 104 of electronic stethoscope 102 to be held against sites on testing surface 210. Horizontal adjuster 204 is shown in FIG. 2 as a simple collar through which horizontal beam 209 may be slid. In this arrangement, the horizontal beam may be locked in place during testing by a set screw, pin, or other standard means. Alternatively, a screw drive, hydraulic, or other system may be used for horizontal adjuster 204, or the horizontal adjuster may be designed to allow horizontal beam 209 to pivot about vertical beam 208. These alternative horizontal adjuster means may be controlled by the computer 116 as part of a testing procedure program, or may be manually controlled. It is also noted that, if electronic stethoscope testing is to be conducted at only one site on testing surface 210, horizontal adjuster 204 may be omitted. Alternatively, it is contemplated that the mounting bracket may be designed to allow movement of the electronic stethoscope sensor in both horizontal dimensions by, for example, adding a second, perpendicular, horizontal beam and adjuster or allowing the horizontal beam to pivot about the vertical beam.

The exemplary embodiment of FIG. 2 includes force meter 206 as part of electronic stethoscope holder 200 to measure the applied force with which sensor 104 is held against testing surface 210 may be controlled. Either spring- and piezoelectric-type force meters may be used. Since vertical (i.e. height) adjuster 202 allows electronic stethoscope holder 200 to be moved as shown by arrows 218, the applied force with which sensor 104 is held against testing surface 210 may be controlled. Vertical adjuster 202 may utilize any of the linear movement systems described above with reference to horizontal adjuster 204. Additionally, piezoelectric control may be used in vertical adjuster 202 to accomplish fine control of applied pressure. As described with reference to horizontal adjuster 204, control of vertical adjuster 202 may be manual or computer based. An output signal from the force meter may be coupled to the computer to allow the applied force to be monitored and/or automatically controlled via signals sent to vertical adjuster 202.

Additionally, vertical controller 202 may be useful for raising electronic stethoscope holder 200 away from test surface 210 to allow horizontal movement of the electronic stethoscope and to simplify coupling and uncoupling of electronic stethoscope sensor 104 to electronic stethoscope holder 200. This may be accomplished by allowing electronic stethoscope holder 200 to be rotated about, or uncoupled from, horizontal beam 209. In this case, horizontal adjuster 202 may be omitted, although it may still be desired to allow adjustment of the applied pressure.

Surface accelerometer 108 is desirably mounted within phantom 100, in contact with test surface 210 as shown. It is desirable for surface accelerometer 108 to be located at the test site to improve the correlation between the electric signal from electronic stethoscope 102 and the surface vibrations measured by surface accelerometer 108. If it is desired to use more than one test site during the testing of an electronic stethoscope, it may be desirable for a separate surface accelerometer to be mounted within the phantom at each test site to be used.

Figure 3:
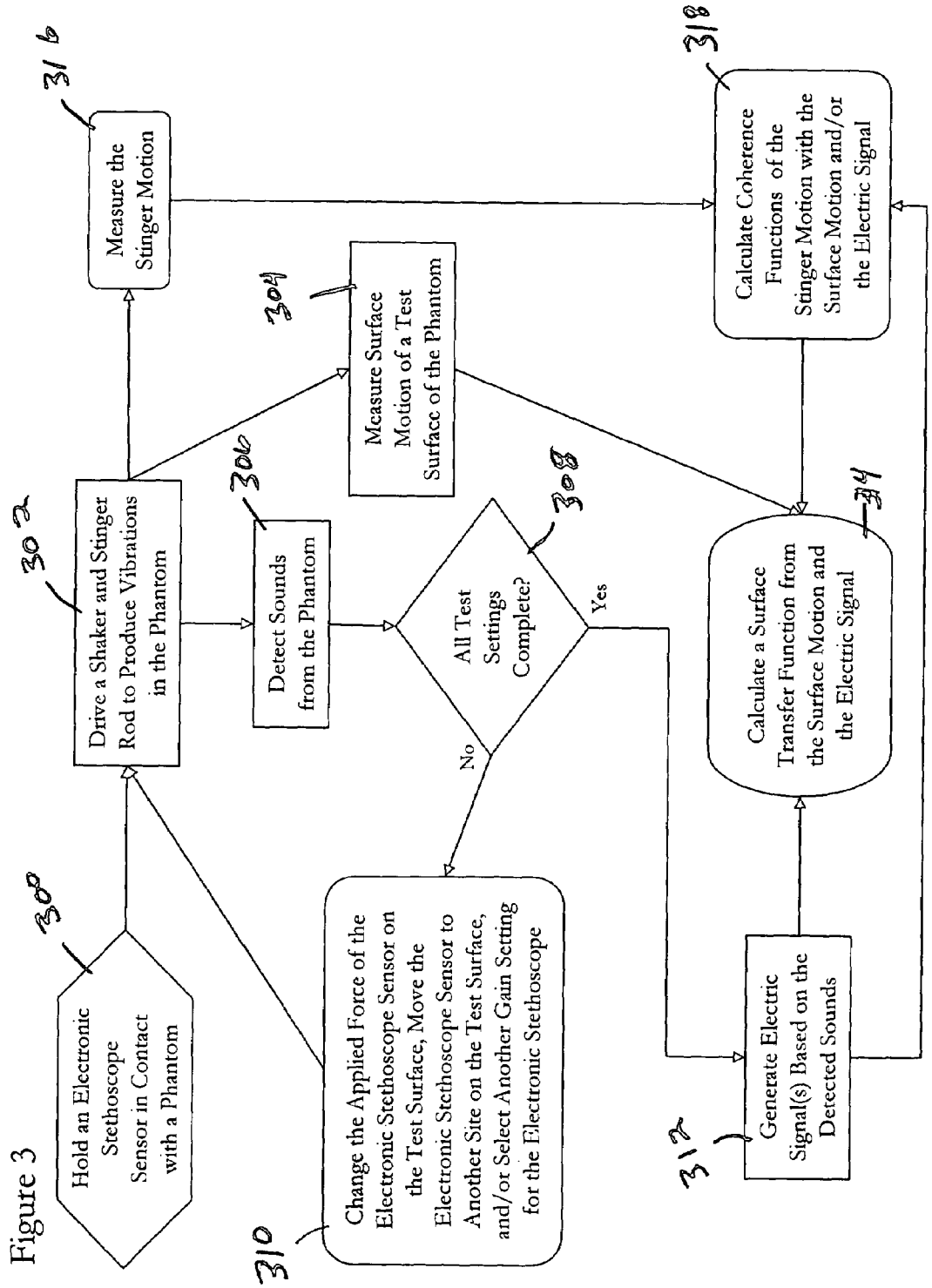
FIG. 3 is a flow chart illustrating an exemplary method of using the system of FIG. 1 according to the present invention.

FIG. 3 is a flowchart which illustrates an exemplary testing procedure for characterizing an electronic stethoscope according to the present invention. The exemplary testing procedure begins with holding the sensor of the electronic stethoscope in contact with a test surface of a phantom, step 300. The applied force of the sensor on the test surface may be measured and may also be adjusted to a predetermined test force. The applied force may be desirably measured with a force meter coupled to the sensor and the applied force then adjusted. Alternatively, the tester may listen to the output of the electronic stethoscope through its earpieces and adjust the applied force to obtain a desirable audio signal from the earpieces.

A shaker, which is coupled to a stinger rod that extends inside the phantom, is driven to produce internal vibrations in the phantom, step 302. The shaker is desirably driven by a signal with a bandwidth large enough to include all frequencies believed to be relevant to the auscultation use for which the electronic stethoscope is being characterized. A continuous, substantially white noise signal with sufficient bandwidth may be used to drive the shaker. Alternatively, a series of signals which together span the desired bandwidth may be used. Additionally, a series of amplitudes may be used to allow characterization of the electronic stethoscope's response to bodily sounds having different volumes.

The surface motion of the test surface of the phantom is measured, step 304. A surface mounted accelerometer with a small enough mass to cause minimal perturbation of the surface motion may desirably be used. Alternatively, a Doppler accelerometer may be reflected off a portion of the test surface to measure surface motion with imperceptible perturbation of the motion. At the same time, an accelerometer mounted to the stinger rod may be used at this time to measure the motion of the stinger rod, i.e. the input vibrations being coupled into the phantom, alternative step 316. Signals representing the motions measured by the accelerometer(s) are transmitted to the computer to be used in analysis of the electronic stethoscope characteristics. Desirably, these signals are scaled to compensate for any known variation in the frequency response of the accelerometers across the desire bandwidth.

Vibrations from the phantom are also detected at this time using the sensor of the electronic stethoscope, step 306. Temporal correlation of the detected phantom vibrations and the surface motions of the test surface may be desirable, but are not strictly necessary. The electronic stethoscope may generate electric signals based on the detected sound, step 312, and transmit the signal to the computer in real time for analysis, or the electronic stethoscope may store the signals to be transmitted following the test run.

If only one set of test parameters is being characterized, then the test setting are complete at decision step 308 and the test sequence proceeds to finish generating and transmitting any remaining electric signals in step 312. Otherwise, at least one of the test parameters is changed, step 310, and the phantom is vibrated, step 302, surface and possibly stinger motion measured, steps 302 and 316, respectively, and vibrations detected by the electronic stethoscope, step 306. Various test parameters may be changed to allow more complete characterization of the electronic stethoscope. Among these parameters are: the applied force of the stethoscope on the test surface; the position of the stethoscope on the test surface; and the gain setting of the electronic stethoscope. Changing the applied pressure of the electronic stethoscope on the test surface may affect the ability of the diaphragm of the stethoscope sensor to vibrate and, thus transform vibrations from the phantom into electric signals.

Moving the stethoscope sensor to various locations on the test surface may allow testing of the stethoscope for different amplitude of phantom vibrations or provide vibrations having slightly different spectral properties due to interference of the sound waves within the phantom. If the electronic stethoscope has multiple gain settings, the preamplifier within the stethoscope may have different gain spectra at each of these settings. Therefore, it may be desirable to characterize the electronic stethoscope at each of these settings.

This cycle of steps 302, 304 and 306 (and possibly 316), 308, and 310, is continued until the test data has been measured for all of the desired test settings. Once it is determined in step 308 that all desired test setting have been used, any electric signals not yet transmitted to the computer are generated and transmitted, step 312.

If the stinger motion has been measured in alternate step 316, then an accelerometer coherence function and/or a stethoscope coherence function may be calculated, alternative step 318, using the formula in Equation (1).

$$\gamma_{xy}^2(f) = \frac{|G_{xy}(f)|^2}{G_{xx}(f)G_{yy}(f)} \quad (1)$$

where $G_{xx}(f)$ is the autospectral density at the input (i.e. the stinger motion signal), $G_{yy}(f)$ is the autospectral density at the output (either the surface motion signal or the electric signal of the electronic stethoscope), and $G_{xy}(f)$ is the cross-spectral density between the input and the output, all as a function of frequency, f. Coherence function values vary between 0 and 1. Values near 1 indicate that minimal noise, nonlinear effects, or other signal degradation is present at that frequency. Values near 0 indicate that measurements at that frequency may be unreliable or that there is poor response at that frequency.

The accelerometer coherence function (based on the stinger motion measured in step 316 and the surface motion measured in step 304) may be used to verify that the test apparatus is working properly and that the results in a given bandwidth are reliable. The stethoscope coherence function (based on the stinger motion measured in step 316 and the electric signal generated in step 306) provide a means of characterizing the quality of the electronic stethoscope response at various frequencies.

Whether these coherence functions are calculated in alternative step 318 or not, a surface transfer function, $H_{steth}(f)$, is calculated to characterize the electronic stethoscope, step 314, using the formula in Equation (2).

$$H_{steth}(f) = \frac{V_{steth}(f)}{V_{surface}(f)} \quad (2)$$

where $V_{steth}(f)$ is the magnitude and phase of the electric signal from the electronic stethoscope and $V_{surfce}(f)$ is the magnitude and phase of the signal from the surface accelerometer.

Although the absolute magnitude of the transfer function at a given frequency is dependent on factors such as the relative gains of amplifiers used the two signals, the relative magnitude of the transfer function between frequencies represents a good characterization of the frequency response of the electronic stethoscope.

It is also contemplated that this method for testing the response of an electronic stethoscope may be used on a special purpose device including a self contained acoustic sensor with associated circuitry, which is intended for use in an automated auscultation system.

Although the invention is illustrated and described herein with reference to specific embodiments, the invention is not intended to be limited to the details shown. Rather, various modifications may be made in the details within the scope and range of equivalents of the claims and without departing from the invention. Specifically, it is contemplated that, although the present invention focuses on the characterization of an electronic stethoscope based on calculating frequency domain relationships, one skilled in the art may understand that the present invention may also be used to calculate other characterizing functions of an electronic stethoscope, such as time domain relationships.

The invention claimed is:

1. A method for characterizing the response of an electronic stethoscope, comprising the steps of:
   a) holding the sensor of the electronic stethoscope in contact with a test surface of a phantom;
   b) inducing internal vibrations in the phantom;
   c) measuring surface motion of the test surface of the phantom using a surface accelerometer coupled to the test surface;
   d) detecting vibrations from the phantom and generating an electric signal based on the detected vibrations with the electronic stethoscope; and
   e) calculating a surface transfer function based on the surface motion measured in step (c) and the electric signal generated in step (d) to characterize the response of the electronic stethoscope.

2. The method according to claim 1 wherein step (a) further includes the step of measuring applied force of the sensor of the electronic stethoscope on the test surface of the phantom.

3. The method according to claim 2 wherein step (a) further includes the step of holding the sensor of the electronic stethoscope such that the applied force of the sensor on the test surface of the phantom approximately equals a predetermined test force.

4. The method according to claim 2 wherein step (d) includes the steps of: d1) detecting vibrations from the phantom with the sensor of the electronic stethoscope held in contact with the test surface of the phantom such that the applied force of the sensor on the test surface of the phantom equals a test force; d2) moving the sensor of the electronic stethoscope such that the applied force of the sensor on the test surface of the phantom equals another test force; and d3) repeating steps (d1) and (d2) until vibrations have been detected at a predetermined number of test forces.

5. The method according to claim 1 wherein step (b) includes the step of driving a shaker coupled to a stinger rod that extends inside the phantom to produce internal vibrations in the phantom.

6. The method according to claim 5 wherein;
   step (b) further includes the step of measuring stinger motion using a stinger accelerometer coupled to the stinger; and
   step (e) further includes the step of further characterizing the response of the electronic stethoscope by calculating at least one of:
      an accelerometer coherence function based on the stinger motion measured in step (b) and the surface motion measured in step (c); and
      a stethoscope coherence function based on the stinger motion measured in step (b) and the electric signal generated in step (d).

7. The method according to claim 1 wherein the internal vibrations are induced in step (b) responsive to at least one of a white noise signal, chirps, and tones.

8. The method according to claim 1 wherein step (d) includes the steps of:
   d1) detecting vibrations from the phantom at a site on the test surface with the electronic stethoscope;
   d2) moving the sensor of the electronic stethoscope to another site on the test surface of the phantom; and
   d3) repeating steps (d1) and (d2) until vibrations have been detected at a predetermined number of sites on the test surface of the phantom.

9. The method according to claim 1 wherein:
   the electronic stethoscope includes a plurality of gain settings; and
   step (d) includes the steps of:
      d1) generating an electric signal based on the detected vibrations with the electronic stethoscope using one of the plurality of gain settings;
      d2) selecting another of the plurality of gain settings of the electronic stethoscope; and
      d3) repeating steps (d1) and (d2) until electric signals have been generated at a predetermined number of the plurality of gain settings of the electronic stethoscope; and
   step (e) includes the step of:
      e1) calculating a separate surface transfer function corresponding to each gain setting selected in step (d) based on the corresponding electric signal.

10. A computer readable medium encoded with instructions to instruct a general purpose computer to characterize the response of an electronic stethoscope, the instructions comprising the steps of: a) generating a test signal to drive a shaker coupled to a stinger rod that extends inside a phantom, whereby internal vibrations are produced in the phantom; b) receiving a motion signal from a surface accelerometer coupled to a test surface of the phantom; c) receiving an electronic stethoscope signal from the electronic stethoscope which is in contact with the test surface of the phantom; and d) calculating a transfer function for the electronic stethoscope based on the motion signal received in step (b) and the electronic stethoscope signal received in step (c).

11. The computer readable medium according to claim 10 wherein the test signal includes at least one of a white noise signal, chirps, and tones.

12. An electronic stethoscope testing apparatus comprising:
   a phantom including a test surface;
   a stinger rod which extends into the interior of the phantom;
   a shaker coupled to the stinger rod to provide vibrations to the phantom;
   a surface accelerometer coupled to the test surface of the phantom to measure movement of the test surface;
   an electronic stethoscope holder coupled to the phantom and arranged to hold a sensor of the electronic stethoscope in contact with the test surface of the phantom; and
   circuitry electrically coupled to the shaker, the surface accelerometer, and the electronic stethoscope to direct and analyze signals provided by the surface accelerometer and the electronic stethoscope.

13. The apparatus according to claim 12, further comprising a stinger accelerometer coupled to the stinger rod and electrically coupled to the circuitry.

14. The apparatus according to claim 12, further comprising a substantially anechoic chamber surrounding the phantom.

15. The apparatus according to claim 12, wherein the phantom has mechanical properties similar to tissue of a thorax.

16. The apparatus according to claim 15, wherein the mechanical properties include density and speed of sound.

17. The apparatus according to claim 15, wherein the phantom is formed of a solid material.

18. The apparatus according to claim 17, wherein the solid material is polyurethane.

19. The apparatus according to claim 15 wherein the phantom is formed of a bladder filled with at least one of a fluid and a gel.

20. The apparatus according to claim 12, wherein the electronic stethoscope holder includes a positioning controller to allow the sensor of the electronic stethoscope to be held in contact with a plurality of sites on the test surface of the phantom.

21. The apparatus according to claim 12, wherein the electronic stethoscope holder includes a height controller to allow adjustment of an applied force of the sensor of the electronic stethoscope on the test surface of the phantom.

22. The apparatus according to claim 12, wherein the electronic stethoscope holder includes a force meter to measure an applied force of the sensor of the electronic stethoscope on the test surface of the phantom.

23. The apparatus according to claim 12, wherein the circuitry includes a general-purpose computer.

24. The apparatus according to claim 12, wherein the circuitry includes one of:
 a spectrum analyzer coupled to the accelerometer and the electronic stethoscope; and
 a digital oscilloscope coupled to the accelerometer and the electronic stethoscope.

25. The apparatus according to claim 12, wherein the circuitry includes at least one of:
 accelerometer preamplifier circuitry coupled to the accelerometer; and
 audio preamplifier circuitry coupled to the electronic stethoscope.

26. The apparatus according to claim 12, wherein the circuitry includes one of:
 a signal generator coupled to the shaker; and
 a white noise generator coupled to the shaker.

27. The apparatus according to claim 26, wherein the circuitry further includes an amplifier coupled to the shaker to amplify a drive signal from the one of the signal generator and the white noise generator.

28. The apparatus according to claim 12, wherein the circuitry includes an analog to digital converter coupled to at least one of the accelerometer and the electronic stethoscope.

* * * * *